(12) United States Patent
Kux et al.

(10) Patent No.: US 7,282,196 B2
(45) Date of Patent: *Oct. 16, 2007

(54) ANTIPERSPIRANT PRODUCT BASED ON MICROEMULSIONS

(75) Inventors: Ulrich Kux, Hamburg (DE); Yvonne Cierpisz, Hamburg (DE); Kurt Mählmann, Neu Wulmstorf (DE); Norbert Menzel, Buchholz (DE); Khiet Hien Diec, Hamburg (DE)

(73) Assignee: Beiersdorf AG, Hamburg (DE)

( * ) Notice: Subject to any disclaimer, the term of this patent is extended or adjusted under 35 U.S.C. 154(b) by 653 days.

This patent is subject to a terminal disclaimer.

(21) Appl. No.: 10/819,781

(22) Filed: Apr. 6, 2004

(65) Prior Publication Data

US 2004/0253187 A1    Dec. 16, 2004

Related U.S. Application Data

(63) Continuation of application No. PCT/EP02/10932, filed on Sep. 30, 2002.

(30) Foreign Application Priority Data

Oct. 6, 2001    (DE)    ................... 101 49 362

(51) Int. Cl.
- A61Q 15/00    (2006.01)
- A61K 8/02    (2006.01)
- A61K 8/06    (2006.01)

(52) U.S. Cl. ................ 424/65; 424/66; 424/68; 424/400; 424/401; 514/937; 514/938; 514/939

(58) Field of Classification Search ............. 424/65, 424/400, 401, 66, 68; 514/937, 938, 939
See application file for complete search history.

(56) References Cited

U.S. PATENT DOCUMENTS

| | | | |
|---|---|---|---|
| 4,530,449 | A | 7/1985 | Nozawa et al. |
| 4,788,001 | A | 11/1988 | Narula |
| 4,935,224 | A | 6/1990 | Russo et al. |
| 5,077,040 | A | 12/1991 | Bergmann et al. |
| 5,388,766 | A | 2/1995 | Buisson |
| 5,487,887 | A | 1/1996 | Benfatto |
| 5,705,562 | A | 1/1998 | Hill |
| 5,707,613 | A | 1/1998 | Hill |
| 5,734,029 | A | 3/1998 | Wulff et al. |
| 5,980,874 | A | 11/1999 | Foerster et al. |
| 6,261,543 | B1 | 7/2001 | Fletcher et al. |
| 6,607,733 | B1 | 8/2003 | Diec et al. |
| 2002/0146375 | A1 | 10/2002 | Schreiber et al. |

FOREIGN PATENT DOCUMENTS

| | | |
|---|---|---|
| DE | 195 09 079 A | 9/1996 |
| DE | 199 56 185 | 5/2001 |
| EP | 0 000 313 A | 1/1979 |
| WO | 95/12379 | 5/1995 |
| WO | WO 96/04940 | 2/1996 |
| WO | 96/23483 | 8/1996 |
| WO | WO 96/28131 | 9/1996 |
| WO | WO 96/28132 | 9/1996 |
| WO | WO 01/24766 A1 | 4/2001 |
| WO | WO 01/58417 A1 | 8/2001 |

OTHER PUBLICATIONS

International Search Report from corresponding International Application No. PCT/EP02/10951 dated Mar. 4, 2003.
International Search Report from corresponding International Application No. PCT/EP02/10932, dated Feb. 5, 2003.
German Search Report dated May 15, 2002.
German Search Report dated May 15, 2002.
Goldschmidt informiert 1982, 57, pp. 22-28 "Herstellung von Mikroemulsionsgelen with TEGO®-Tensiden" (Preparation of Microemulsion Gels with TEGO® Surfactants).
Happi, Feb. 1993, pp. 58, 60, 62 and 64, "Microemulsion Gels: A Formulators Guide".

*Primary Examiner*—Shelley A. Dodson
(74) *Attorney, Agent, or Firm*—Greenblum & Bernstein, P.L.C.

(57) ABSTRACT

The present invention is an antiperspirant product, comprising:
(a) an oil-in water microemulsion including an oil phase and a water phase and being substantially free of alcohol, said microemulsion further comprising:
one or more oil-in-water emulsifiers selected from the group consisting of polyethoxylated oil-in-water emulsifiers, polypropoxylated oil-in-water emulsifiers and polyethoxylated and polypropoxylated oil-in-water emulsifiers, wherein said microemulsion has a total emulsifier content of less than 20% by weight, based on the total weight of the microemulsion, and
one or more antiperspirants, having a total content of 5 to 40% by weight, based on the total weight of the microemulsion,
wherein said microemulsion is prepared by bringing a mixture comprising the water phase, the oil phase, and the one or more oil-in-water emulsifiers to a temperature within or above the phase-inversion temperature range, and subsequently cooling it to room temperature, and
(b) a pump atomizer, comprising:
a container, and
an atomizer pump comprising a riser tube, a cylindrical chamber which is placed under pressure by depressing a piston, a pump valve which closes the cylindrical chamber and opens under a pressure of at least 0.7 mPa, and two or more turbulence channels radiating to a nozzle opening, said channels causing a flowing liquid to rotate relative to a flow axis.

22 Claims, No Drawings

ANTIPERSPIRANT PRODUCT BASED ON MICROEMULSIONS

CROSS-REFERENCE TO RELATED APPLICATIONS

This is a continuation application of PCT/EP02/10932, filed Sep. 30, 2002, which is incorporated herein by reference in its entirety, and also claims the benefit of German Priority Application No. 101 49 362.2, filed Oct. 6, 2001.

FIELD OF THE INVENTION

The present invention relates to a cosmetic deodorant product which is a combination of packaging and application means and a thin-liquid oil-in-water microemulsion with a high content of antiperspirant salt, and can be applied evenly with the help of an atomizer pump.

BACKGROUND OF THE INVENTION

The human skin is covered with two to three million sweat glands. These are used day and night to convey moisture to the surface of the skin and thus to prevent the organism from overheating. The sweat which emerges ensures the necessary cooling as it evaporates.

In the normal case, 0.5 to 1 liter of sweat are produced daily. In cases of strain on the body and increased metabolism, it may be many times the amount of produced sweat. The course of the development of a human involves the formation of two types of sweat glands. From birth onwards, a person has only ecrine sweat glands (small sweat glands) but the onset of puberty sees the formation of the apocrine sweat glands (large sweat glands), primarily in the area of the armpits and in the anal and genital regions. Only the latter lead, in connection with skin bacteria which decompose the odorless sweat, to the known unpleasant odors. The odor of sweat is person-specific and is pronounced to different degrees for each person. For most people, simple washing can only achieve a short-term improvement, meaning that often enough it is not possible without the use of deodorant active ingredients.

In order to achieve a deodorant effect, there are various ways which, in the normal case, are used in combination.

The use of antiperspirants which prevent the production of sweat by blocking the openings of sweat glands has been known for a long time. Use is usually made here of aluminum and aluminum/zirconium salts. According to the latest findings, the reduced sweat production has no effect on the organism since the "cooling effect" largely takes place via the "sweating" of the other areas of the skin (ecrine glands). The inhibition of bacterial growth as a result of bacteriostats in the area of the skin zones covered with apocrine sweat glands is not acceptable and sometimes leads to severe irritations and allergic reactions.

The alcohol (ethanol) which is present in many of the conventional deodorant products also acts as bacteriocide. Here too, side-effects are often common.

To mask the odor of sweat, fragrances or perfume substances are usually present in the deodorant preparations. Some of these also have a bacteriostatic effect, but with many of them users have similar side-effects as the bacteriostats.

Due to the mode of action described above and the side-effects associated therewith, the attempts to develop deodorant products which do not have side-effects are great. The trend is thus clearly in the direction of a combination product in which a deodorizing and antiperspirant effect accompanies a skincare effect.

Such care deodorants based on O/W (oil-in-water) emulsions have already entered the market, but handling, that is to say application to the skin, still leaves a lot to be desired.

For the application of antiperspirants, many consumers favor the so-called pump atomizer product form since the contents can be applied from this in finely dispersed form to the armpit region without the fingers having to come into contact with them. Compared with aerosols, there is also the ecological advantage that pump atomizers function without the use of propellants (liquefied gases). Transparent and translucent products are preferred by many consumers primarily for aesthetic reasons. The combination of this feature with the wish for highly effective antiperspirant products has hitherto only been realized with aqueous alcohol formulations. These formulations consist virtually only of water and alcohol as medium, deodorant and antiperspirant agents as active ingredients, and perfume, solubility promoters and thickeners (in most cases based on carbohydrate) as additional agents. They are perceived by the consumer as being fresh and cooling, but are at the same time burdened with a whole series of shortcomings. For example, the application primarily to freshly shaved skin is associated with incompatibilities as a result of the alcohol content. A further significant disadvantage is the fact that relatively large amounts of oil cannot be incorporated into such systems. As a result of the high content of antiperspirant salt required for a highly effective performance, a white residue remains on the skin following application, which is perceived as highly undesirable by the consumer. As a result of the absence, brought about technologically, of a sufficiently large oil phase however, this cannot be concealed. Moreover, the use of carbohydrate thickeners leads to a certain stickiness of the product after the alcohol has evaporated. In summary, it may be said that aqueous alcohol formulations are not suitable as a base for the incorporation of high contents of antiperspirant agents (aluminum or aluminum/zirconium complexes).

The solution to all of these disadvantages has been a long time coming. Only recently have also cosmetically pleasing alcohol-free-transparent products been possible which are based on so-called microemulsions. These have the great advantage that even relatively large amounts of various oils—with all of the above-described positive effects for the consumer—can be stably incorporated. Formulations of this type are in principle obtainable by means of phase-inversion temperature technology (PIT) or high-pressure homogenization. The necessary stability of the emulsifier system to high concentrations of antiperspirant salts, however, places high requirements on the formulating skill of the product developer. The use of microemulsions in the cosmetic sector is described in detail in EP 0814752.

For the application of antiperspirants, many consumers favor the product form of the so-called pump atomizer which allows the contents to be applied from it to the armpit region in finely distributed form without the fingers having to be brought into contact with it. Compared with aerosols, there is also the ecological advantage that pump atomizers do not use propellants (liquefied gases). However, a uniform drop size and even spray image cannot be achieved using conventional atomizer pumps since many formulations with a high content of antiperspirant agents, especially ones based on an aqueous alcohol base, have a tendency to form crystals when the atomizer is not often used and represent a high risk of blockage for the nozzle. This hinders or prevents the product from coming out. On the other hand, the consequence of excessively large drops is the running down of the formulation (dripping effect), as a result of which the application is perceived as unpleasantly wet and troublesome.

SUMMARY OF THE INVENTION

The object of the present invention is therefore to enrich the prior art and to overcome its disadvantages.

Surprisingly, it has been found that the use of atomizer pumps with a high ratio of precompression to the application amount leads to a conical spray image with uniformly fine droplets. This ensures targeted application in the armpit and prevents the coalescence to form large, escaping drops.

In the case of the use of atomizers according to the invention, by operating the atomizer pump, the liquid to be atomized in the cylindrical chamber is placed under pressure and "precompressed" by depressing a piston. If the precompression reaches a pressure of about 0.7 MPa, a pump valve opens and the liquid can flow in the direction of the nozzle. Here, the liquid is pressed by two or more turbulence channels radiating to a cylindrical nozzle opening and atomized following passage through the nozzle opening. Precompression means the pressure which has to be built up in order to open the valve to the outside world and to spray the contents through the nozzle. Since it is a gas-free system, the compression is not equated with a change in volume, but a dynamic pressure increase. The turbulence channels cause the flowing liquid to rotate about the flow axis.

As a result of the increased initial pressure compared with normal atomizer pumps, with which the contents are forced through the exit nozzle, and the special combination of low-volatility preparation constituents, blockage of the nozzle is prevented. As a result, the use of the emulsion formulations described below with an increased antiperspirant content is also possible since any crystals, residues and encrustations which arise in the region of the nozzle are forced away by the high spray pressure.

The spray image remains even throughout the entire spray operation—the time of which is determined by the period over which the piston is depressed—since the above-described valve acts as a type of safety valve and only opens at a corresponding pre-pressure and thus the spray pressure does not change over the entire period.

The atomizers according to the invention have a very low operating force and, compared to normal atomizers, small spray volumes. The mode of action of the small spray volume is superior to that of conventional atomizers as a result of the very uniform and fine spray image.

Surprisingly, in the base formulation for the abovementioned objects it is possible to use alcohol-free transparent or translucent microemulsions of the oil-in-water type,
  comprising an oil phase and a water phase,
  comprising:
  one or more polyethoxylated O/W emulsifiers,
  one or more polypropoxylated O/W emulsifiers, and/or
  one or more polyethoxylated and polypropoxylated O/W emulsifiers,
  if desired also comprising one or more W/O (water-in-oil) emulsifiers,
  having an emulsifier content of less than 20% by weight, based on the total weight of the emulsion,
  having an antiperspirant content of from 5 to 40% by weight, in particular from 7 to 25% by weight, based on the total weight of the emulsion,
  obtainable by bringing a mixture of the basic components comprising water phase, oil phase, one or more of the O/W emulsifiers according to the invention, if desired one or more W/O emulsifiers, and if desired further auxiliaries, additives or active ingredients to a temperature within or above the phase-inversion temperature range, and subsequently cooling it to room temperature, as described in EP 0814752, in an excellent manner for antiperspirant products.

DETAILED DESCRIPTION OF THE PREFERRED EMBODIMENTS

Microemulsions according to the invention have a low viscosity, are sprayable, are especially suitable as vehicles for a very wide variety of active ingredients, in particular lipid-soluble active ingredients and, moreover, are characterized by excellent skin and mucosa compatibility.

All of the constituents—apart from water and fragrances—of the microemulsion according to the invention are of low volatility, i.e., in the pure state they have a low vapor pressure at 25° C., as a result of which drying up and crystal formation upon regular use of the atomizer is suppressed.

It is advantageous for the purposes of the invention when the oil phase of the oil-in-water emulsion has a droplet size less than 100 nm.

The polyethoxylated, polypropoxylated or polyethoxylated and polypropoxylated O/W emulsifier(s) are advantageously chosen from the group of:
  fatty alcohol ethoxylates of the general formula R—O—(—$CH_2$—$CH_2$—O—)$_n$—H, where R is a branched or unbranched alkyl, aryl or alkenyl radical and n is a number from 10 to 50,
  ethoxylated wool wax alcohols,
  polyethylene glycol ethers of the general formula R—O—(—$CH_2$—$CH_2$—O—)$_n$—R', where R and R', independently of one another, are branched or unbranched alkyl or alkenyl radicals and n is a number from 10 to 80,
  fatty acid ethoxylates of the general formula R—COO—(—$CH_2$—$CH_2$—O—)$_n$—H, where R is a branched or unbranched alkyl or alkenyl radical and n is a number from 10 to 40,
  etherified fatty acid ethoxylates of the general formula R—COO—(—$CH_2$—$CH_2$—O—)$_n$—R', where R and R', independently of one another, are branched or unbranched alkyl or alkenyl radicals and n is a number from 10 to 80,
  esterified fatty acid ethoxylates of the general formula R—COO—(—$CH_2$—$CH_2$—O—)$_n$—C(O)—R', where R and R', independently of one another, are branched or unbranched alkyl or alkenyl radicals and n is a number from 10 to 80,
  polyethylene glycol glycerol fatty acid esters of saturated or unsaturated, branched or unbranched fatty acids and a degree of ethoxylation between 3 and 50,
  ethoxylated sorbitan esters with a degree of ethoxylation of from 3 to 100,
  cholesterol ethoxylates with a degree of ethoxylation between 3 and 50,
  ethoxylated triglycerides with a degree of ethoxylation between 3 and 150,
  alkyl ether carboxylic acids of the general formula R—O—(—$CH_2$—$CH_2$—O—)$_n$—$CH_2$—COOH or cosmetically or pharmaceutically acceptable salts thereof, where R is a branched or unbranched alkyl or alkenyl radical having 5-30 carbon atoms and n is a number from 5 to 30,
  polyoxyethylene sorbitol fatty acid esters based on branched or unbranched alkanoic or alkenoic acids and having a degree of ethoxylation of from 5 to 100, for example of the sorbeth type, alkyl ether sulfates or the acids on which the sulfates are based of the general formula R—O—(—CH$_2$—CH$_2$—O—)$_n$—SO$_3$—H with cosmetically or pharmaceutically acceptable cations, where R is a branched or unbranched alkyl or alkenyl radical having 5-30 carbon atoms and n is a number from 1 to 50, fatty alcohol propoxylates of the general formula R—O—(—CH$_2$—CH(CH$_3$)—O—)$_n$—H, where R is a branched or unbranched alkyl or alkenyl radical and n is a number from 10 to 80, polypropylene glycol ethers of the general formula R—O—(—CH$_2$—CH(CH$_3$)—O—)$_n$—R', where R and R', independently of one another, are branched or unbranched alkyl or alkenyl radicals and n is a number from 10 to 80, propoxylated wool wax alcohols, etherified fatty acid propoxylates of the general formula R—COO—(—CH$_2$—CH(CH$_3$)—O—)$_n$—R', where R and R', independently of one another, are branched or unbranched alkyl or alkenyl radicals and n is a number from 10 to 80, esterified fatty acid propoxylates of the general formula R—COO—(—CH$_2$—CH(CH$_3$)—O—)$_n$—C(O)—R', where R and R', independently of one another, are branched or unbranched alkyl or alkenyl radicals and n is a number from 10 to 80, fatty acid propoxylates of the general formula R—COO—(—CH$_2$—CH(CH$_3$)—O—)$_n$—H, where R is a branched or unbranched alkyl or alkenyl radical and n is a number from 10 to 80, polypropylene glycol glycerol fatty acid esters of saturated or unsaturated, branched or unbranched fatty acids and a degree of propoxylation between 3 and 80, propoxylated sorbitan esters with a degree of propoxylation of from 3 to 100, cholesterol propoxylates with a degree of propoxylation of from 3 to 100, propoxylated triglycerides with a degree of propoxylation of from 3 to 100, alkyl ether carboxylic acids of the general formula R—O—(—CH$_2$—CH(CH$_3$)O—)$_n$—CH$_2$—COOH or cosmetically or pharmaceutically acceptable salts thereof, where R is a branched or unbranched alkyl or alkenyl radical and n is a number from 3 to 50, alkyl ether sulfates or the acids on which the sulfates are based of the general formula R—O—(—CH$_2$—CH(CH$_3$)—O—)$_n$—SO$_3$—H with cosmetically or pharmaceutically acceptable cations, where R is a branched or unbranched alkyl or alkenyl radical having 5-30 carbon atoms and n is a number from 1 to 50, fatty alcohol ethoxylates/propoxylates of the general formula R—O—X$_n$—Y$_m$—H, where R is a branched or unbranched alkyl or alkenyl radical, where X and Y are not identical and are in each case either an oxyethylene group or an oxypropylene group and n and m, independently of one another, are numbers from 5 to 50, polypropylene glycol ethers of the general formula R—O—X$_n$—Y$_m$—R', where R and R', independently of one another, are branched or unbranched alkyl or alkenyl radicals, where X and Y are not identical and are in each case either an oxyethylene group or an oxypropylene group and n and m, independently of one another, are numbers from 5 to 100, etherified fatty acid propoxylates of the general formula R—COO—X$_n$—Y$_m$—R', where R and R', independently of one another, are branched or unbranched alkyl or alkenyl radicals, where X and Y are not identical and are in each case either an oxyethylene group or an oxypropylene group and n and m, independently of one another, are numbers from 5 to 100, and fatty acid ethoxylates/propoxylates of the general formula R—COO—X$_n$—Y$_m$—H, where R is a branched or unbranched alkyl or alkenyl radical, where X and Y are not identical and are in each case either an oxyethylene group or an oxypropylene group and n and m, independently of one another, are numbers from 5 to 50.

It is particularly advantageous when the polyethoxylated, polypropoxylated or polyethoxylated and polypropoxylated O/W emulsifier(s) are chosen from the group of fatty alcohol ethoxylates of the general formula R—O—(—CH$_2$—CH$_2$—O—)$_n$—H, where R is a branched or unbranched alkyl or alkenyl radical having 5-30 carbon atoms and n is a number from 10 to 25, ethoxylated wool wax alcohols with HLB values of 11-16, very particularly advantageously with HLB values of 14.5-15.5, polyethylene glycol ethers of the general formula R—O—(—CH$_2$—CH$_2$—O—)$_n$—R', where R and R', independently of one another, are branched or unbranched alkyl or alkenyl radicals having 5-30 carbon atoms and n is a number from 10 to 25, fatty acid ethoxylates of the general formula R—COO—(—CH$_2$—CH$_2$—O—)$_n$—H, where R is a branched or unbranched alkyl or alkenyl radical having 5-30 carbon atoms and n is a number from 10 to 25, etherified fatty acid ethoxylates of the general formula R—COO—(—CH$_2$—CH$_2$—O—)$_n$—R', where R and R', independently of one another, are branched or unbranched alkyl or alkenyl radicals having 5-30 carbon atoms and n is a number from 10 to 50, esterified fatty acid ethoxylates of the general formula R—COO—(—CH$_2$—CH$_2$—O—)$_n$—C(O)—R', where R and R', independently of one another, are branched or unbranched alkyl or alkenyl radicals having 5-30 carbon atoms and n is a number from 10 to 50, polyethylene glycol glycerol fatty acid esters of saturated or unsaturated, branched or unbranched fatty acids having 6 to 26 carbon atoms and a degree of ethoxylation between 3 and 40, ethoxylated sorbitan esters with a degree of ethoxylation of from 3 to 30, cholesterol ethoxylates with HLB values of 11-16, very particularly advantageously with HLB values of 14.5-15.5, ethoxylated triglycerides with HLB values of 11-16, very particularly advantageously with HLB values of 14.5-15.5, alkyl ether carboxylic acids of the general formula R—O—(—CH$_2$—CH$_2$—O—)$_n$—CH$_2$—COOH or cosmetically or pharmaceutically acceptable salts thereof, where R is a branched or unbranched alkyl or alkenyl radical having 5-30 carbon atoms and n is a number from 10 to 20, polyoxyethylene sorbitol fatty acid esters based on branched or unbranched alkanoic or alkenoic acids and having a degree of ethoxylation of from 10 to 80, for example of the sorbeth type, alkyl ether sulfates or acids on which the sulfates are based of the general formula R—O—(—CH$_2$—CH$_2$—O—)$_n$—SO$_3$—H with cosmetically or pharmaceutically acceptable cations, where R is a branched or unbranched alkyl or alkenyl radical having 5-30 carbon atoms and n is a number from 3 to 30, fatty alcohol propoxylates of the general formula R—O—(—CH$_2$—CH(CH$_3$)—O—)$_n$—H, where R is a branched or unbranched alkyl or alkenyl radical having 5-30 carbon atoms and n is a number from 10 to 30, polypropylene glycol ethers of the general formula R—O—(—CH$_2$—CH(CH$_3$)—O—)$_n$—R', where R and R', independently of one another, are branched or unbranched alkyl or alkenyl radicals having 5-30 carbon atoms and n is a number from 10 to 40, propoxylated wool wax alcohols with HLB values of 11-16, very particularly advantageously with HLB values of 14.5-15.5, fatty acid propoxylates of the general formula R—COO—(—CH$_2$—CH(CH$_3$)—O—)$_n$—H, where R is a branched or unbranched alkyl or alkenyl radical having 5-30 carbon atoms and n is a number from 10 to 40, etherified fatty acid propoxylates of the general formula R—COO—(—CH$_2$—CH(CH$_3$)—O—)$_n$—R', where R and R', independently of one another, are branched or unbranched alkyl or alkenyl radicals having 5-30 carbon atoms and n is a number from 10 to 30, esterified fatty acid propoxylates of the general formula R—COO—(—CH$_2$—CH(CH$_3$)—O—)$_n$—C(O)—R', where R and R', independently of one another, are branched or unbranched alkyl or alkenyl radicals having 5-30 carbon atoms and n is a number from 10 to 50, polypropylene glycol glycerol fatty acid esters of saturated or unsaturated, branched or unbranched fatty acids having from 6 to 26 carbon atoms and a degree of propoxylation between 3 and 50, propoxylated sorbitan esters with a degree of propoxylation of from 3 to 80, cholesterol propoxylates with HLB values of 11-16, very particularly advantageously with HLB values of 14.5-15.5, propoxylated triglycerides with HLB values of 11-16, very particularly advantageously with HLB values of 14.5-15.5, alkyl ether carboxylic acids of the general formula R—O—(—CH$_2$—CH(CH$_3$)O—)$_n$—CH$_2$—COOH or cosmetically or pharmaceutically acceptable salts thereof, where R is a branched or unbranched alkyl or alkenyl radical having 5-30 carbon atoms and n is a number from 10 to 30, and alkyl ether sulfates or the acids on which the sulfates are based of the general formula R—O—(—CH$_2$—CH(CH$_3$)—O—)$_n$—SO$_3$—H with cosmetically or pharmaceutically acceptable cations, where R is a branched or unbranched alkyl or alkenyl radical having 5-30 carbon atoms and n is a number from 1 to 30.

According to the invention, the polyethoxylated, polypropoxylated or polyethoxylated and polypropoxylated O/W emulsifiers used are particularly advantageously chosen from the group of substances with HLB values of 11-16, very particularly advantageously with HLB values of 14.5-15.5 if the O/w emulsifiers have saturated radicals R and R'. If the O/W emulsifiers have unsaturated radicals R or R', or if isoalkyl derivatives are present, then the preferred HLB value of such emulsifiers may also be lower or higher.

It is advantageous to choose the fatty alcohol ethoxylates from the group of ethoxylated stearyl alcohols, cetyl alcohols, and cetylstearyl alcohols (cetearyl alcohols). Particular preference is given to: polyethylene glycol(13) stearyl ether (steareth-13), polyethylene glycol(14) stearyl ether (steareth-14), polyethylene glycol(15) stearyl ether (steareth-15), polyethylene glycol(16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20), polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20), polyethylene glycol(13) cetyl ether (ceteth-13), polyethylene glycol(14) cetyl ether (ceteth-14), polyethylene glycol(15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20), polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20), polyethylene glycol(12) oleyl ether (oleth-12), polyethylene glycol(13) oleyl ether (oleth-13), polyethylene glycol(14) oleyl ether (oleth-14), polyethylene glycol(15) oleyl ether (oleth-15), polyethylene glycol(12) lauryl ether (laureth-12), polyethylene glycol(12) isolauryl ether (isolaureth-12), polyethylene glycol(13) cetylstearyl ether (ceteareth-13), polyethylene glycol(14) cetylstearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol(19) cetylstearyl ether (ceteareth-19), and polyethylene glycol(20) cetylstearyl ether (ceteareth-20).

It is also advantageous to choose the fatty acid ethoxylates from the following group: polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, and polyethylene glycol(20) oleate.

The ethoxylated alkyl ether carboxylic acid or salt thereof which can be used advantageously is sodium laureth-11 carboxylate.

Sodium laureth-14 sulfate can be used advantageously as alkyl ether sulfate.

The ethoxylated cholesterol derivative which can be used advantageously is polyethylene glycol(30) cholesteryl ether. Polyethylene glycol(25) soyasterol has also proven useful.

The ethoxylated triglycerides which can be used advantageously are polyethylene glycol(60) evening primrose glycerides.

It is also advantageous to choose the polyethylene glycol glycerol fatty acid esters from the group consisting of polyethylene glycol(20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate, polyethylene glycol(20) glyceryl oleate, polyethylene glycol(20) glyceryl isostearate, and polyethylene glycol(18) glyceryl oleate/cocoate.

It is likewise favorable to choose the sorbitan esters from the group consisting of polyethylene glycol(20) sorbitan monolaurate, polyethylene glycol(20) sorbitan monostearate, polyethylene glycol(20) sorbitan monoisostearate, polyethylene glycol(20) sorbitan monopalmitate, and polyethylene glycol(20) sorbitan monooleate.

The W/O emulsifiers which are optional but advantageous according to the invention which may be used are: fatty alcohols having 8 to 30 carbon atoms, monoglycerol esters of saturated or unsaturated, branched or unbranched alkanecarboxylic acids with a chain length of from 8 to 24, in particular 12-18, carbon atoms, diglycerol esters of saturated or unsaturated, branched or unbranched alkanecarboxylic acids with a chain length of from 8 to 24, in particular 12-18, carbon atoms, monoglycerol ethers of saturated or unsaturated, branched or unbranched alcohols with a chain length of from 8 to 24, in particular 12-18, carbon atoms, diglycerol ethers of saturated or unsaturated, branched or unbranched alcohols with a chain length of from 8 to 24, in particular 12-18, carbon atoms, propylene glycol esters of saturated or unsaturated, branched or unbranched alkanecarboxylic acids with a chain length of from 8 to 24, in particular 12-18, carbon atoms, and sorbitan esters of saturated or unsaturated, branched or unbranched alkanecarboxylic acids with a chain length of from 8 to 24, in particular 12-18, carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprate, and glyceryl monocaprylate.

It is possible according to the invention to keep the total content of emulsifiers less than 20% by weight, based on the total weight of the microemulsion. It is preferred to keep the total content of emulsifiers less than 15% by weight, in particular less than 10% by weight, based on the total weight of the microemulsion.

The oil phase of the microemulsions according to the invention is advantageously chosen from the group of esters of saturated or unsaturated, branched or unbranched alkanecarboxylic acids with a chain length of from 3 to 30 carbon atoms and saturated or unsaturated, branched or unbranched alcohols with a chain length of from 3 to 30 carbon atoms, and from the group of esters of aromatic carboxylic acids and saturated or unsaturated, branched or unbranched alcohols with a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In addition, the oil phase can advantageously be chosen from the group of branched and unbranched hydrocarbons and hydrocarbon waxes, of silicone oils, of dialkyl ethers, the group of saturated or unsaturated, branched or unbranched alcohols, and also the fatty acid triglycerides, namely the triglycerol esters of saturated or unsaturated, branched or unbranched alkanecarboxylic acids with a chain length of from 8 to 24, in particular 12-18, carbon atoms. The fatty acid triglycerides can, for example, advantageously be chosen from the group of synthetic, semisynthetic and natural oils, e.g. olive oil, sunflower oil, soybean oil, groundnut oil, rapeseed oil, almond oil, palm oil, coconut oil, palm kernel oil and the like.

Any mixtures of such oil and wax components can also be used advantageously for the purposes of the present invention.

It may also in some cases be advantageous to use waxes, for example cetyl palmitate, as the sole lipid component of the oil phase. In such cases, the O/W microemulsions according to the invention may also in some cases be formed as microdispersions of solid wax particles.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride and dicaprylyl ether.

Particularly advantageous mixtures are those of $C_{12-15}$-alkyl benzoate and 2-ethylhexyl isostearate, mixtures of $C_{12-15}$-alkyl benzoate and isotridecyl isononanoate, and mixtures of $C_{12-15}$-alkylbenzoate, 2-ethylhexyl isostearate and isotridecyl isononanoate.

Of the hydrocarbons, paraffin oil, squalane and squalene are to be used advantageously for the purposes of the present invention.

The oil phase can advantageously also have a content of cyclic or linear silicone oils, or consist entirely of such oils, although it is preferable to use an additional content of other oil phase components apart from the silicone oil or the silicone oils.

Advantageously, cyclomethicone (decamethylcyclopentasiloxane) is used as the silicone oil to be used according to the invention. However, other silicone oils are also to be used advantageously for the purposes of the present invention, for example hexamethylcyclotrisiloxane, octamethylcyclotetrasiloxane, polydimethylsiloxane, and poly(methylphenylsiloxane).

Also particularly advantageous are mixtures of cyclomethicone and isotridecyl isononanoate, and those of cyclomethicone and 2-ethylhexyl isostearate.

The microemulsions according to the invention are advantageously prepared by bringing a mixture of the basic components, comprising water phase, oil phase, one or more of the O/W emulsifiers according to the invention, if desired one or more W/O emulsifiers, and if desired further auxiliaries, additives or active ingredients, which form an O/W emulsion below the phase-inversion temperature range, to a temperature above or within the phase-inversion temperature range, and consequently cooling the formed microemulsion to room temperature. This is preferably carried out with stirring.

Surprisingly, it is in each case possible to dispense with a homogenization step.

Advantageously, large amounts of acidic aluminum and/or aluminum/zirconium salts can be stably incorporated into the emulsions. 5 to 40% by weight, in particular 7 to 25% by weight, of aluminum chlorohydrate and/or aluminum/zirconium chlorohydrate can be stably incorporated into the emulsions. In this connection, the described concentration ranges refer to the so-called active contents of the antiperspirant complexes: in the case of the aluminum compounds to anhydrous complexes, in the case of the aluminum/zirconium compounds to anhydrous and buffer-free complexes. The buffer used here is usually glycine.

The subsequent listing of antiperspirant agents to be used advantageously should in no way be limiting:

Aluminum salts (of the empirical formula $[Al_2(OH)_mCl_n]$, where m+n=6):
- aluminum salts, such as aluminum chloride $AlCl_3$, aluminum sulfate $Al_2(SO_4)_3$
- aluminum chlorohydrate $[Al_2(OH)_5Cl]$ x $H_2O$ standard Al complexes: Locron L (Clariant), Chlorhydrol (Reheis), ACH-303 (Summit), Aloxicoll L (Giulini). activated Al complexes: Reach 501 (Reheis), MCH-324 (Summit)
- aluminum sesquichlorohydrate $[Al_2(OH)_{4.5}Cl_{1.5}] \times H_2O$ standard Al complexes: aluminum sesquichlorohydrate (Reheis), ACH-308 (Summit), Aloxicoll 31 L (Giulini) activated Al complexes: Reach 301 (Reheis)
- aluminum dichlorohydrate $[Al_2(OH)_4Cl_2] \times H_2O$ Aluminum/zirconium salts:
- aluminum/zirconium trichlorohydrex glycine $[Al_4Zr(OH)_{13}Cl_3] \times H_2O \times Gly$ standard Al/Zr complexes: Rezal 33GP (Reheis), AZG-7164 (Summit), Zirkonal P3G (Giulini) activated Al/Zr complexes: Reach AZZ 902 (Reheis), AAZG-7160 (Summit), Zirkonal AP3G (Giulini)
- aluminum/zirconium tetrachlorohydrex glycine $[Al_4Zr(OH)_{12}Cl_4]$ $\times H_2O \times Gly$ standard Al/Zr complexes: Rezal 36G (Reheis), AZG-368 (Summit), Zirkonal L435G (Giulini) activated Al/Zr complexes: Reach AZP 855 (Reheis), AAZG-6313-15 (Summit), Zirkonal AP4G (Giulini)
- aluminum/zirconium pentachlorohydrex glycine $[Al_8Zr(OH)_{23}Cl_5]$ $\times H_2O \times Gly$ standard Al/Zr complexes: Rezal 67 (Reheis), Zirkonal L540 (Giulini) activated Al/Zr complexes: Reach AZN 885 (Reheis)
- aluminum/zirconium octachlorohydrex glycine $[Al_8Zr(OH)_{20}Cl_8]$ $\times H_2O \times Gly$.

Glycine-free aluminum/zirconium salts may, however, also likewise be advantageous.

In this connection, the use of the antiperspirant agents from the raw material classes of aluminum and aluminum/zirconium salts should not be limited to the standard commercial mainly aqueous solutions, such as, for example, Locron L (Clariant), but it may also be advantageous to use the likewise standard commercial anhydrous powders of the same raw materials by incorporation into the claimed formulations, such as, for example, Locron P (Clariant).

The use of so-called AT-salt suspensions in which aluminum and aluminum/zirconium salts present in powder form are supplied dispersed in various oils could also be advantageous.

Furthermore, it may, however, also be advantageous to use special aluminum and aluminum/zirconium salts which are supplied for improving the solubility as glycol complexes.

Further advantageous antiperspirant agents are based, instead of on aluminum or zirconium, on other metals, such as, for example, beryllium, titanium and hafnium.

In this connection, the list of antiperspirant agents which can be used should, however, not be limited to metal-containing raw materials, but compounds which comprise nonmetals, such as boron, and those which are classed as being in the field of organic chemistry, such as, for example, anticholergics, are also advantageous. Advantageous in this sense are also polymers which may either contain metals or be metal-free.

The effect arising in numerous preparations of a visible white residue remaining on the skin following application of the preparation is usually perceived by the user as being undesirable. In anhydrous preparations, the use of propoxylated alcohols has proven useful for concealing this phenomenon. In the case of water-containing preparations, no satisfactory solution to this problem is hitherto known. The addition of propoxylated alcohols having 10 to 20 propyloxy units and 2 to 10 carbon atoms in the alkyl chain, in particular PPG-14 butyl ether, as constituent of the medium-polar oil phase overcomes the described shortcoming of the prior art reliably concealing the appearance of such white residues.

Deodorants can advantageously be added to preparations according to the invention. Customary cosmetic deodorants are based on various activity principles.

The use of antimicrobial substances in cosmetic deodorants can reduce the bacterial flora on the skin. In this connection, in the ideal case, only the odor-causing microorganisms should be effectively reduced. The flow of sweat itself is not influenced by this, and in an ideal case only microbial decomposition of the sweat is temporarily stopped. The combination of astringents with antimicrobially effective substances in one and the same composition is also customary.

All active ingredients customary for deodorants may be used advantageously, for example odor concealers, such as the customary perfume constituents, odor absorbers, for example the sheet silicates described in DE 40 09 347, and of these, in particular, montmorillonite, kaolinite, illite, beidellite, nontronite, saponite, hectorite, bentonite, smectite, and also, for example, zinc salts of ricinoleic acid. Antimicrobial agents are likewise suitable for incorporation into the emulsions according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the effective agents described in DE 37 40 186, DE 39 38 140, DE 42 04 321, DE 42 29 707, DE 42 29 737, DE 42 37 081, DE 43 09 372 and DE 43 24 219. Sodium hydrogencarbonate can also be used advantageously.

The list of said active ingredients or active ingredient combinations which can be used in the emulsions according to the invention is not of course intended to be limiting. The amount of deodorants (one or more compounds) in the preparations is preferably 0.01 to 10% by weight, particularly preferably 0.05 to 5% by weight, in particular 0.1 to 1% by weight, based on the total weight of the preparation.

Preparations according to the invention can also additionally comprise hydrocolloids, inorganic pigments, antioxidants or cosmetic or dermatological active ingredients, which may either be oil-soluble or water-soluble.

The cosmetic and dermatological preparations according to the invention can comprise cosmetic auxiliaries, as are customarily used in such preparations, e.g. preservatives, bactericides, perfumes, antifoams, dyes, pigments which have a coloring action, thickeners, moisturizing or humectant substances, fats, oils, waxes or other customary constituents of a cosmetic or dermatological formulation, such as alcohols, polyols, polymers, foam stabilizers, organic solvents or silicone derivatives, and moisturizers.

The examples below serve to illustrate the present invention without limiting it. Unless stated otherwise, all of the amounts, fractions and percentages are based on the weight and the total amount or on the total weight of the preparations.

EXAMPLE FORMULATIONS

Translucent microemulsion formulae:

| Chemical name | INCI | No. 1 | No. 2 | No. 3 | No. 4 |
|---|---|---|---|---|---|
| Polyoxyethylene(20) cetylstearyl ether | Ceteareth-20 | 3 | 4 | 5 | 4 |
| Polyoxyethylene(12) cetylstearyl ether | Ceteareth-12 | 0.5 | — | — | — |
| Glycerol stearate | Glyceryl stearate | 3 | 3 | 2 | — |
| Glycerol isostearate | Glyceryl isostearate | — | — | — | 3 |
| Cetylstearyl alcohol | Cetearyl alcohol | 0.5 | — | — | — |
| Cetyl palmitate | Cetyl palmitate | 0.5 | — | — | — |
| Cetyl alcohol | Cetyl alcohol | — | 2 | — | 1 |
| Stearyl alcohol | Stearyl alcohol | — | — | 2 | — |
| Caprylic-capric ester | Coco-caprylate/caprate | 5 | 3 | 3 | 4 |
| Di-n-octyl ether | Dicaprylyl ether | 5 | — | 5 | 4 |
| Di-n-octyl carbonate | Dicaprylyl carbonate | — | 3 | — | 1 |
| Glycerol | Glycerol | 4 | 2 | 3 | 3 |
| Aluminum chlorohydrate (50% aq. soln.) | Aluminum chlorohydrate | 16 | 30 | 40 | 20 |
| 3,7,11-trimethyl-2,6,10-dodecatrien-1-ol | Farnesol | 1 | — | — | 1 |
| Octyldodecanol | Octyldodecanol | — | 1 | 1 | — |
| Avocado oil | Persea Gratissima | 1 | 1 | 1 | — |
| Glycerol laurate | Glyceryl laurate | 1 | — | 1 | — |
| Perfume | Perfume | 1 | 1 | — | — |
| Water, ad | Aqua, ad | 100 | 100 | 100 | 100 |

Transparent microemulsion formulae:

| Chemical name | INCI | No. 5 | No. 6 | No. 7 | No. 8 |
|---|---|---|---|---|---|
| Glycerol monoisostearate | Glyceryl isostearate | 3 | 2 | 3 | 4 |
| Polyoxyethylene-20 isohexadecyl ether | Isoceteth-20 | 6 | 5 | — | — |
| Polyoxyethylene-20 isooctadecyl ether | Isosteareth-20 | — | — | 6 | — |
| Polyoxyethylene-25 octyldodecyl ether | Octyldodeceth-25 | — | — | — | 5 |
| Caprylic-capric ester | Coco-caprylate/caprate | — | 5 | 3 | 5 |
| Di-n-octyl ether | Dicaprylyl ether | 5 | — | — | — |
| Di-n-octyl carbonate | Dicaprylyl carbonate | — | 3 | 5 | 3 |
| Glycerol | Glycerol | — | 4 | 3 | 3 |
| Butylene glycol | Butylene glycol | 3 | — | — | — |
| Aluminum chlorohydrate (50% aq. soln.) | Aluminum chlorohydrate | 16 | 20 | 40 | 30 |
| 3,7,11-trimethyl-2,6,10-dodecatrien-1-ol | Farnesol | 1 | — | 1 | — |
| Avocado oil | Persea Gratissima | — | 1 | — | 1 |
| Octyldodecanol | Octyldodecanol | — | 1 | — | 1 |
| Glycerol laurate | Glyceryl laurate | — | 1 | — | 1 |
| Glycerol monocaprate | Glyceryl caprate | 1 | — | 1 | — |
| Jojoba oil | Buxus Chinensis | 1 | — | 1 | — |
| Perfume | Perfume | 1 | 1 | — | 1 |
| Water, ad | Aqua, ad | 100 | 100 | 100 | 100 |

That which is claimed:

1. An antiperspirant product, comprising:
   (a) an oil-in water microemulsion comprising an oil phase and a water phase and being substantially free of alcohol, the microemulsion further comprising:
   one or more oil-in-water emulsifiers selected from polyethoxylated oil-in-water emulsifiers, polypropoxylated oil-in-water emulsifiers and polyethoxylated and polypropoxylated oil-in-water emulsifiers, wherein said microemulsion has a total emulsifier content of less than 20% by weight, based on a total weight of the microemulsion, and
   one or more antiperspirants, having a total content of 5% to 40% by weight, based on the total weight of the microemulsion,
   wherein said microemulsion is prepared by bringing a mixture comprising the water phase, the oil phase, and the one or more oil-in-water emulsifiers to a temperature within or above the phase-inversion temperature range, and subsequently cooling it to room temperature, and
   (b) a pump atomizer, comprising:
   a container, and
   an atomizer pump comprising a riser tube, a cylindrical chamber which is placed under pressure by depressing a piston, a pump valve which closes the cylindrical chamber and opens under a pressure of at least 0.7 MPa, and two or more turbulence channels radiating to a nozzle opening, said channels causing a flowing liquid to rotate relative to a flow axis.

2. The antiperspirant product of claim 1, wherein the microemulsion is alcohol-free.

3. The antiperspirant product of claim 1, wherein the microemulsion is transparent or translucent.

4. The antiperspirant product of claim 1, wherein the microemulsion has an antiperspirant content of from 7% to 25% by weight.

5. The antiperspirant product of claim 1, wherein the microemulsion further comprises one or more of auxiliaries, additives and active ingredients.

6. The antiperspirant product of claim 1, wherein the oil phase has a droplet size of less than 100 nm.

7. The antiperspirant product of claim 1, wherein the one or more antiperspirants comprise one or more acidic salts.

8. The antiperspirant product of claim 7, wherein the one or more acidic salts are selected from one or more of acidic aluminum salts and acidic aluminum/zirconium salts.

9. The antiperspirant product of claim 8, wherein and a total amount of the one or more of acidic aluminum salts and aluminum/zirconium salts is at least 5% by weight, based on the total weight of the microemulsion.

10. The antiperspirant product of claim 1, wherein a total amount of polyethoxylated oil-in-water emulsifiers is from 0.1% to 8% by weight, based on the total weight of the microemulsion.

11. The antiperspirant product of claim 1, wherein a total amount of polyethoxylated oil-in-water emulsifiers is from 0.5% to 6.5% by weight, based on the total weight of the microemulsion.

12. The antiperspirant product of claim 1, wherein a total amount of polyethoxylated oil-in-water emulsifiers is from 1% to 5% by weight, based on the total weight of the microemulsion.

13. The antiperspirant product of claim 1, wherein a total amount of polypropoxylated oil-in-water emulsifiers is from 0.1% to 8% by weight, based on the total weight of the microemulsion.

14. The antiperspirant product of claim 1, wherein a total amount of polypropoxylated oil-in-water emulsifiers is from 0.5% to 6.5% by weight, based on the total weight of the microemulsion.

15. The antiperspirant product of claim 1, wherein a total amount of polypropoxylated oil-in-water emulsifiers is from 1% to 5% by weight, based on the total weight of the microemulsion.

16. The antiperspirant product of claim 1, wherein a total amount of polyethoxylated and polypropoxylated oil-in-water emulsifiers is from 0.1% to 8% by weight, based on the total weight of the microemulsion.

17. The antiperspirant product of claim 1, wherein a total amount of polyethoxylated and polypropoxylated oil-in-water emulsifiers is from 0.5% to 6.5% by weight, based on the total weight of the microemulsion.

18. The antiperspirant product of claim 1, wherein a total amount of polyethoxylated and polypropoxylated oil-in-water emulsifiers is from 1% to 5% by weight, based on the total weight of the microemulsion.

19. The antiperspirant product of claim 1, wherein the microemulsion further comprises one or more water-in-oil emulsifiers.

20. The antiperspirant product of claim 19, wherein a total amount of the one or more water-in-oil emulsifiers is from 0.1% to 5% by weight, based on the total weight of the microemulsion.

21. The antiperspirant product of claim 19, wherein a total amount of the one or more water-in-oil emulsifiers is from 0.5% to 3.5% by weight, based on the total weight of the microemulsion.

22. The antiperspirant product of claim 19, wherein a total amount of the one or more water-in-oil emulsifiers is from 1% to 2.5% by weight, based on the total weight of the microemulsion.

* * * * *